United States Patent [19]

Gersonde et al.

[11] 4,452,747

[45] Jun. 5, 1984

[54] METHOD OF AND ARRANGEMENT FOR PRODUCING LIPID VESICLES

[76] Inventors: Klaus Gersonde, Preusweg 69, D-5100 Aachen; Wilfried Schäl, Tannenwaldweg 27, D-6380, Bad Homburg, both of Fed. Rep. of Germany

[21] Appl. No.: 360,173

[22] Filed: Mar. 22, 1982

[51] Int. Cl.³ .................... B01J 13/02; B01F 11/02
[52] U.S. Cl. ........................... 264/4.1; 73/570; 252/359 B; 424/38; 424/94; 428/402.2; 436/829
[58] Field of Search ............... 264/4.1, 4.3; 424/38; 428/402.2; 73/570; 252/359 B; 436/829

[56] References Cited

U.S. PATENT DOCUMENTS

| 4,016,100 | 4/1977 | Suzuki et al. .................. 264/4.3 |
| 4,192,869 | 3/1980 | Nicolau et al. ................ 424/343 X |
| 4,372,949 | 2/1983 | Kodama et al. ................ 424/38 X |

FOREIGN PATENT DOCUMENTS

| 2338503 | 2/1974 | Fed. Rep. of Germany . |
| 526819 | 8/1976 | U.S.S.R. .................. 73/570 |
| 684329 | 9/1979 | U.S.S.R. .................. 73/570 |

Primary Examiner—Richard D. Lovering

[57] ABSTRACT

In accordance with a method of and an arrangement for producing lipid vesicles from biological membranes or lipid suspensions, a lipid suspension or lipid particles in a dispersion fluid are accommodated in a treatment container, ultrasonic treatment of the same is performed in condition of a substantially constant temperature, ultrasonic frequency and intensity for providing a desirable size or size distribution of the lipid vesicles are determined, and these parameters are maintained constant by measuring an actual value of frequency and intensity of an ultrasonic field of the reaction medium and adjusting a power and frequency of the ultrasonic treatment in dependence upon the measured actual value.

27 Claims, 2 Drawing Figures

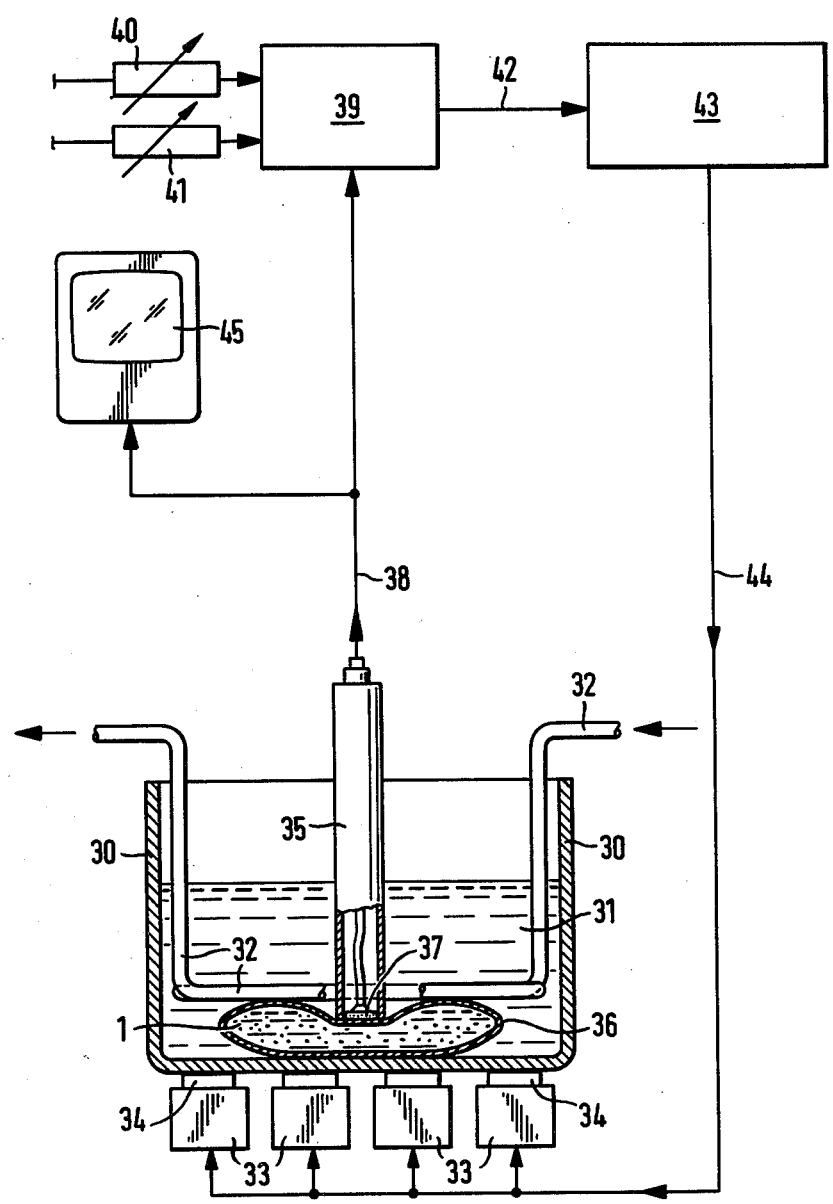

METHOD OF AND ARRANGEMENT FOR PRODUCING LIPID VESICLES

BACKGROUND OF THE INVENTION

The present invention relates to a method of and arrangement for producing uniform, unilamellar so-called small lipid vesicles, particularly for conversion of lamellarly arranged lipids into lipid vesicles.

Methods and arrangement of the above mentioned general type are known in the art. Lipid structures such as lamellae are accommodated in a suspension fluid inside a container and subjected to an ultrasonic treatment in condition of a constant temperature. Lipid vesicles are utilized, for example, for medical therapy and for basic research purposes. Drugs or effectors which control the intracellular metabolism and having intracellular receptors and binding-sites need to penetrate into the cell from outside. Many effectors normally formed inside the cell can neither leave the cell nor the surrounding medium. The therapeutic use of the substances of this class makes necessary to provide a transport mechanism which allows the irreversible incorporation of these non-membrane-permeable substances into the cells, namely without any possibility to leave the cells after this process. Such a transport mechanism must be, moreover, as independent as possible from the effector to be incorporated, i.e. it allows incorporation of effectors of any type, on the one hand, and should be cell-specific, i.e., allows the incorporation of effectors only in predetermined cells, on the other hand. A transport system with the above mentioned properties is provided by lipid vesicles which can include different substances, such as enzymes, drugs, chelate-forming substances, hormones, cell-effectors, antigenes, antibodies, interferon inductors and genes. In the lipid vesicles, the solvent and the substance dissolved in the solvent are enclosed by phospholipid bilayer membrane. The lipid membrane has a thickness of typically 4 nm, and the vesicles can have a diameter from 25 to 120 nm. The size of the vesicles can be determined by the laser light scattering, ultracentrifugation, gel-filtration or electron scanning microscopy.

An important field of application of the lipid vesicles is the incorporation of inositolhexaphosphate (IHP) into red blood cells (RBC) in accordance with the method described by Y. C. Nicolau and K. Gersonde, one of the instant co-inventors, in U.S. Pat. No. 4,192,869, for reducing the oxygen affinity of the intracellular hemoglobin. It is known that during storage of blood preserves, the oxygen affinity of the hemoglobin in the red cells is continuously increased. Furthermore during certain diseases an increased oxygen affinity of the hemoglobin can also be observed. This increased oxygen affinity is the reason that only a small portion of oxygen which is bound to the hemoglobin and circulated in the blood, is effectively released to the tissues. This high oxygen affinity of the hemoglobin can be reduced by binding certain effectors to the hemoglobin. The strongest effector of this type is the inositol hexaphosphate (IHP). The incorporation of IHP is attained in such a manner that the intact cells are incubated with IHP-loaded lipid vesicles and that by fusion of the lipid membrane of the cells and the vesicles IHP is incorporated into the cells where it is bound to hemoglobin and changes the oxygen affinity of the hemoglobin measurable by "right-shifting" of the hemoglobin-oxygen dissociation curve. After retransfusion of these IHP-loaded red blood cells into the blood vessels, a considerably greater portion of the oxygen stored in the red blood cells is released to the peripheral tissues. This property of the treated red blood cells is retained during the entire life of the cells.

For incorporation of the inositol hexaphosphate into red blood cells, small unilamellar IHP-loaded lipid vesicles with a diameter from 20 to 50 nm are required. It is known to produce lipid vesicles by disintegration of lipid suspensions in an ultrasonic field. The progress in the utilization of lipid vesicles was, however, very slow because the production of lipid vesicles suitable for fusion with the red blood cells in a satisfactory quantity is accompanied by considerable difficulties. The lipid vesicles suitable for this purpose must not only be produced in sufficient quantities, but also must be reproducible in identical sizes and thereby dosable in the therapeutic administration. The subsequent use of separation procedures for isolating suitable fractions of the particular lipid vesicles encounters many problems, for example maintaining of sterility and utilization of expensive and time-consuming separation techniques considerably reducing the biological effectiveness of the vesicles which have at room temperature a half-life of approximately one day. The only method which can produce large quantities of vesicles in short time is the ultrasonic disintegration technique.

In addition to the type and composition of the lipid vesicles, the success and the reproducibility of experimental work or of a therapeutic treatment, i.e. incorporation of IHP in red blood cells, depend essentially on the size of lipid vesicles. The verification, whether or not the disintegration of the lipid suspension produces lipid vesicles of sufficient homogeneity and thereby of good quality and in sufficient quantity, is generally performed in such a manner that with the produced lipid vesicles the desired IHP uptaken by red blood cells is controlled by chemically detecting the intracellular IHP, and by measuring the hemoglobin-oxygen dissociation curve of intact cells or by quantifying the desirable biological or therapeutic action of the IHP-loaded red blood cells in animal tests. The yield of IHP-loaden vesicles and the effectiveness of the treatment of red blood cells can only be evaluated after expensive and time-consuming experiments. The result of the ultrasonic preparation, namely the production of the vesicles suitable for fusion with red blood cells, can be evaluated only afterwards.

It has been shown that the production of lipid vesicles, particularly in large volumes, as required for therapeutic processes, with constantly maintained properties with the aid of the ultrasonic technique is difficult. Despite preservation of completely identical outer conditions during the disintegration of the lipid suspensions in the ultrasonic field, it was not possible to attain the uniform production of so-called small unilamellar and thereby fusion-active lipid vesicles.

SUMMARY OF THE INVENTION

Accordingly, it is an object of the present invention to provide a method of and an arrangement for producing lipid vesicles, which avoid the disadvantages of the prior art.

More particularly, it is an object of the present invention to provide a method of and an arrangement for producing lipid vesicles, which provide for incorporation of effectors into cells and are further developed so that the efficiency thereof is increased and a high yield of highly active lipid vesicles for desired purposes takes place in a reproducible manner.

In keeping with these objects and with others which will become apparent hereinafter, one feature of the present invention resides, briefly stated, in a method and an arrangement in which the vesicle size or vesicle size distribution for the desired purpose, as well as the optimal ultrasonic frequency and intensity required for obtaining of a particular vesicle size or size distribution is determined, and the thus determined optimal ultrasonic frequency and intensity, with the other constant conditions, are maintained in such a manner that during the ultrasonic treatment the actual frequency and intensity of the ultrasonic field in the reaction medium is continuously measured and the frequency and output power of ultrasonic generating means is adjusted in dependence upon these actual parameters. More particularly, the frequency and output power of an electric generator supplied to a sound transmitter is adjusted.

The invention is based upon the recognition that during the utilization of the vesicles for therapeutic purposes, the size or size distribution of the vesicles are of exclusive importance for the action thereof, on the one hand, and the size and homogeneity of the vesicles produced in the ultrasonic field intimately depend on the constancy and intensity of the ultrasonic field acting upon the lipids. While it is known to measure and to maintain the electric energy supplied to the sound transmitter, the invention resides in that the effective sound energy of the reaction medium is measured and purposely changed so that the effective sound energy in the reaction medium is automatically maintained at its optimal value. By measuring the effective sound energy in the reaction medium and by the utilization of the actual value for adjusting the generated sound energy, there are compensated all effects which influence the effective sound intensity and the sound frequency at the location of vesicle formation. More particularly, there are compensated different and changeable absorption of the sound energy with progressing reaction, changing geometrical conditions inside the reaction medium during formation of gas bubbles under the action of the ultrasonic treatment, as well as the effect of reflected ultrasound waves which are superimposed with the sound waves emitted by the sound transmitter, and in some cases during phase-shifting leads to extinguishing of the sound energy.

In accordance with the present invention, at first the optimal vesicle diameter or the optimal distribution curve of the effective diameter are determined by known methods, then in a further set of experiments the optimal ultrasonic conditions such as frequency and sound pressure are determined which lead to the desired distribution curve, and finally the thus obtained optimal ultrasonic intensity and ultrasonic frequency inside the reaction medium is maintained during the reaction time. Thereby a very high yield of lipid vesicles which are specifically effective for the respective purpose is achieved.

The method according to the invention allows not only the production of lipid vesicles, but also provides for treatment of natural biological membranes and their conversion into vesicles, for example during investigation of structure and function of membrane-enzymes. In this case it is also required to convert the membrane-enzymes into vesicles of a predetermined size in an reproducible manner, which is not possible by the known methods with sufficient reliability.

The novel features of the present invention are set forth in the appended claims. The invention itself, however, will be best understood from the following description of preferred embodiments, which is accompanied by the following drawings.

BRIEF DESCRIPTION OF THE DRAWINGS

FIG. 2 is a sectional view schematically showing an arrangement suitable for producing lipid vesicle suspensions in sterile packages for clinical use, in accordance with the present invention.

DESCRIPTION OF THE PREFERRED EMBODIMENTS

Figure 1:
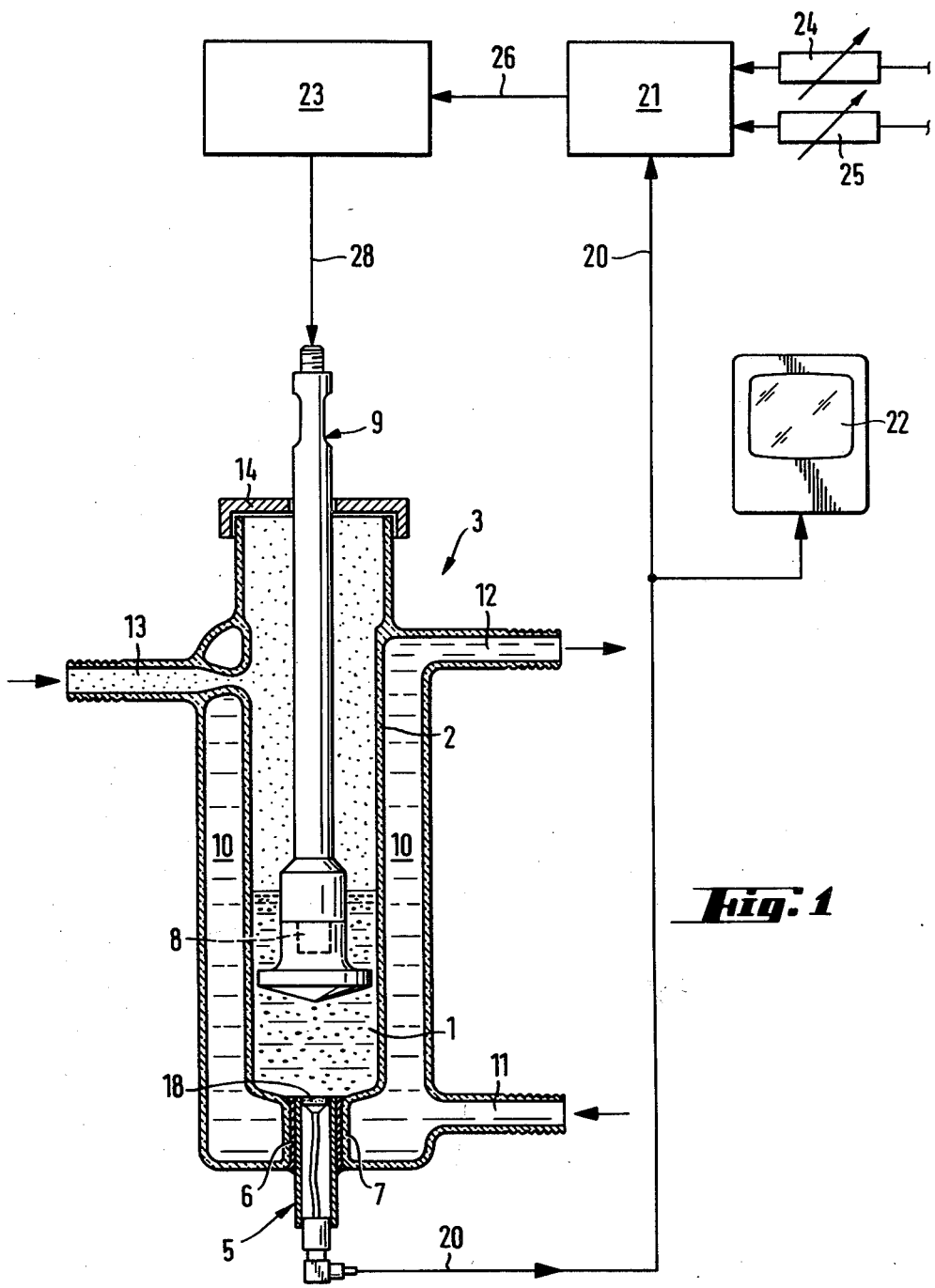
FIG. 1 is a sectional view schematically showing an arrangement suitable for producing relatively small quantities of lipid vesicle suspensions, in accordance with the present invention.

A reaction medium 1 in form of a suspension of a lipid in a suitable dispersion medium is accommodated in an inner cylinder-shaped tube 2 of a double-wall glass reaction container 3. A bottom of the reaction container 3 has a through going opening which opens into a reaction chamber. A sound receiver 5 is inserted into the opening of the bottom. The sound receiver 5 is glued and sealed with the aid of an epoxy resin layer 6 to a wall 7 of the opening. An ultrasonic vibration transmitter 8 is introduced into the reaction medium 1 from above. The vibration transmitter 8 has an upper part 9 extending outwardly beyond the reaction container 3 and provided with a coupling 9 to a current source.

The double walls of the reaction container form a hollow space lo through which a cooling water circulates. Pipes 11 and 12 serve for supplying and withdrawing the cooling water. A pipe 13 leads into the reaction chamber above the reaction medium and serves for supplying an inert gas such as argon. The reaction chamber is closed at the top by a cover 14. The inert gas which is under a small pressure can escape through a gap remaining between the cover 14 and the ultrasonic transmitter or the container wall.

The sound receiver 5 has at its upper end which is in contact with the reaction medium 1, a sound pressure or sound intensity detector formed as a disk of piezo-electric ceramic material 18. The piezo disk 18 is built, in the shown example, radially in a holding tube, and is glued and sealed in the latter by epoxy resin. An electric signal supplied by the piezo disk 18 is a measure for an effective sound frequency and the effective sound intensity. This electrical signal forms an actual value of a control or adjustment circuit and is supplied via a conductor 20 to a control amplifier 21. From an oscilloscope 22, the effective frequency and the sound intensity can be observed, and if necessary, manual adjustment of the frequency and the power of a high-frequency generator 23 can be carried out. The control amplifier 21 is provided with a nominal value of the ultrasonic intensity via a normal value adjusting device 24, and with a nominal value of the ultrasonic frequency via a nominal value adjusting device 25. In the event of deviation of the actual value of the frequency and the intensity of the ultrasonic field in the reaction medium from the given nominal values the ultrasonic generator 23 is controlled or adjusted via a conductor 26, and its frequency and/or power is changed until the effective values measured in the reaction medium 1 coincide with the given nominal values. The ultrasonic transmitter is supplied with the required electric voltage by the high-frequency generator via conductor 28.

An arrangement shown in FIG. 2 is suitable for production of lipid vesicles in greater quantities. The reaction container is formed as an upwardly open rectangular vessel 30 of corrosion-resistant Cr-Ni steel. For cooling a liquid 31 in the reaction container, a cooling hose 32 is introduced into the liquid 31 accommodated in the vessel 30. Eight electroacoustic transducers 33 are arranged on the bottom of the vessel 30 at its outer side and connected with vibration transmitters 34. The sound energy is thus transmitted to the liquid 31 in the vessel 30. A sound receiver 35 is inserted into the liquid 31 from above. The reaction medium is accommodated in a closed sterile bag 36 which is retained above the bottom of the tank by the cooling hose 32 inside the liquid 31. The sound receiver 35 is dipped to such a depth that a sound receiver head, i.e. a piezo disk 37 is pressed against the sterile bag 36, whereby the ultrasonic field acting upon the reaction medium is measured.

The signal supplied from the piezo disk 37 controls or adjusts a control amplifier 39 via a conductor 38 and provides for an actual value for the controlling or adjusting process. The nominal values for the ultrasonic frequency and intensity are given by nominal value devices 40 and 41. In the event of deviation of the actual values from the nominal values, an adjustable electric generator 43 is adjusted via a conductor 42. The electric generator adjusts the power and/or frequency of the electromagnetic transducers 33 via a conductor 44 until the nominal value and the actual value coincide with one another. The frequency and amplitude of the ultrasonic field measured by the piezo disk 37 can be visually observed on an oscilloscope 45 so that the manual adjustment can also be performed.

With the aid of the above described arrangement, the following reactions can, for example, be performed:

EXAMPLE 1

This example relates to the production of IHP-loaded lipid vesicles for therapeutic purposes, namely for incorporating IHP into red blood cells by fusion for improving oxygen release capacity of the red blood cells. The general method of preparation of lipid vesicles is described in the U.S. Pat. No. 4,192,869, to which references are made here. The lipid vesicles are formed from phosphatidylcholine, phosphatidylserine and cholesterol in molar ratio of 8:2:7. These lipids are first dissolved in an organic solvent of 95 parts of chloroform and 5 parts of methanol in order to provide for a homogenous solution and mixture. Then the solvent is removed at 20° C. in a rotary evaporizer. The lipid film remaining in the round flask is mixed and shaked with an aqueous solution containing the biologically active substance (here IHP), so that flat lipid lamellae are formed in this suspension. This suspension contains lipids with a concentration of approximately 17-200 μg per ml. The suspension is further saturated with IHP and buffered between pH 7.0-8.0. In a preceding set of tests, it was determined that for the fusion with erythrocytes and the incorporation of IHP into erythrocytes, vesicles are suitable which have the above mentioned composition and a diameter of 250-500 Å. The greater the quantity of this effective type of vesicles is in the respective preparation, the greater will be the effect. By a further set of tests it was determined that this desired diameter distribution can be attained when the lipid is subjected to sound treatment in condition of a substantially constant temperature of 37° C. with a small-band sound frequency of 20 kHz and with an effective sound energy of 3 to 6 W per square cm. It should be noted that these data refer to a specific experimental set-up and may be different if certain conditions are changed.

The above described lipid suspension is filled into the reaction container 3 under the inert gas. The reaction container is sweeped via the pipe 13 with argon. On the nonimal value adjustment devices 24 and 25, the optimal sound intensity and the desired sound frequency are then adjusted The described control or adjusting device acts so that the optimal sound intensity is effectively acting upon the reaction liquid, during the entire treatment time. The treatment continues for 30-60 minutes. During this time, heat generated in the reaction container is withdrawn by the cooling water and the temperature is maintained constant.

The thus produced vesicle suspension is now incubated with red blood cells at 37° C. for 1 hour. Then the red blood cells are washed in isotonic buffer with pH 7.4, and the hemoglobinoxygen dissociation curve of modified intact cells is measured. The results of the IHP incorporation is recognized as "right shift" of the hemoglobin-oxygen dissociation curve. The maximum oxygen half-saturation pressure obtained by IHP-binding of hemoglobin, amounts to 95 mm Hg at 37° C. and pH 7.4.

The success of the controllable ultrasonic method is based, first of all, on the result that the maximum IHP incorporation effect can be obtained with such volume ratios, RBC (red blood cells): vesicles, or vesicle concentrations, which must be only 10% of the lipid concentration taking place in conventional uncontrolled ultrasonic treatment for IHP incorporation. This provides for a considerable advantage, since lipids are expensive and cannot be repeatedly utilized. Moreover, in the known methods no reproducible results can be obtained, which is an indispensible condition for a reliable dosing in the therapy.

EXAMPLE 2

For therapeutic use the lipid vesicles must satisfy the requirement of absolute sterility. Since a sterilization of the prepared vesicle suspension encounters extreme difficulties, the following process is utilized: The inital components corresponding to those of Example 1 are first sterilized and supplied in sterile condition into a sterilized bag of polyethylene or soft PVC foil with a wall thickness of approximately 0.5 mm. The bag is sterile-tightly closed and then subjected to the ultrasonic action in the container of FIG. 2, whereas the space between the container walls and the bag is filled with water. The measuring of the sound intensity is performed in this case at the surface of the bag. With the same operation as in the Example 1, the same results will be obtained when the power supplied to the sound transmitters is increased by approximately a factor of 1.65. This factor obtained from the tests of the inventive arrangement represents the power losses caused by immersing of the bag.

We wish it to be understood that we do not desire to be limited to the exact details of construction shown and described, for obvious modifications will occur to a person skilled in the art.

Having thus described the invention, what we claim as new and desire to be protected by Letters Patent is as follows:

1. In a method of producing lipid vesicles from biological membranes or lipid suspensions by ultra-sonic treatment,
the steps comprising,
accommodating a reaction medium including a lipid suspension or lipid particles in a dispersion fluid inside a treatment container;
establishing a closed control loop, including generating high-frequency electric energy, converting the high frequency electric energy into ultrasonic energy, transmitting the ultrasonic energy into said reaction medium for treatment of the medium and controlling said high frequency electric energy;
determining the optimum ultrasonic frequency and intensity of said ultrasonic energy for providing a desirable size parameter of the lipid vesicles;
maintaining the determined optimum ultrasonic frequency and intensity constant by continuously measuring the actual value of the frequency and intensity of the ultrasonic energy in the reaction medium, and adjusting the intensity and frequency of the ultrasonic treatment in dependence upon the thus measured actual value.

2. A method as defined in claim 1, wherein said determining step includes determining the ultrasonic frequency and intensity for providing a desirable size of the lipid vesicles.

3. A method as defined in claim 1, wherein said determining step includes determining the ultrasonic frequency and intensity for providing a desirable size distribution of the lipid vesicles.

4. A method as defined in claim 1, wherein said ultrasonically treating step includes producing vibrations by an ultrasonic transmitter supplied from an electric generator, said adjusting step including adjusting an output power and frequency of the electric generator.

5. A method as defined in claim 4, wherein said adjusting step includes adjusting the output power and frequency of the generator with the aid of an adjusting circuit including an actual value-nominal value comparator.

6. A method as defined in claim 4, wherein said measuring step includes measuring the frequency and intensity of the ultrasonic field with the aid of a piezoelectric sound receiver dipped into the reaction medium.

7. A method as defined in claim 6, wherein said measuring step includes dipping the ultrasound transmitter into the upper third of the reaction medium, and arranging the piezoelectric sound receiver on a bottom of the container so that the direction of a maximum sensitivity of the sound receiver is directed against the ultrasound transmitter.

8. A method as defined in claim 1, wherein said ultrasonic treating step includes treating in an inert gas atmosphere.

9. A method as defined in claim 1, wherein said accommodating step includes sterilizing the reaction medium, accommodating the same in the treatment container formed as a sterile bag, and arranging the sterile bag with the reaction medium inside a further container filled with a fluid exposed to ultrasonic vibrations during said treating step.

10. A method as defined in claim 1, further comprising the steps of
sterilizing said lipide suspension or lipide particles,
supplying a sterilized bag normally disposed in said container with said sterilized lipide suspension or lipide particles, and
closing said sterilized bag in a sterile-tight manner, prior to treating the lipide suspension or lipide particles by said ultrasound waves.

11. A method of producing lipide vesicles for therapeutical purposes loaded with an effective substance and capable of fusing with red blood cells, from biological membranes or lipide suspensions, comprising the steps of
determining the optimum ultrasonic frequency and intensity of said ultrasound waves for providing a desirable size parameter of the lipide vesicles;
accommodating a reaction medium including a lipide suspension or lipide particles in a dispersion fluid inside a treatment container;
establishing a closed control loop, including generating high frequency electric energy, converting the high frequency electric energy into ultrasonic energy, transmitting the ultrasonic energy into said reaction medium, measuring the effective ultrasonic energy in the reaction medium and controlling said high frequency electric energy;
treating the lipide suspension or lipide particles in the container at a substantially constant temperature; and
maintaining the determined optimum ultrasonic frequency and intensity constant by measuring the actual value of the frequency and intensity of the ultrasonic field in the reaction medium in the container and adjusting the power and frequency of the ultrasonic treating in dependence upon the thus measured actual value.

12. A method of producing lipid vesicles for therapeutical purposes loaded with inositol hexaphosphate and capable of fusing with red blood cells, from biological membranes or lipid suspensions, comprising the steps of
accommodating a reaction medium including a lipid suspension or lipid particles in a dispersion fluid inside a treatment container;
ultrasonically treating the lipid suspension or lipid particles in the container in condition of a substantially constant temperature;
determining the optimum ultrasonic frequency and intensity for providing a desirable size parameter of the lipid vesicles; and
maintaining the thus determined optimum ultrasonic frequency and intensity constant by measuring the actual value of the frequency and intensity of the ultrasonic field in the reaction medium in the container and adjusting the power and frequency of the ultrasonic treating in dependence upon the thus measured actual value.

13. An arrangement for producing lipid vesicles from biological membranes or lipid suspensions,
comprising in combination,
a treatment container arranged to accommodate a reaction medium including a lipid suspension or lipid particles in a dispersion fluid;
means for establishing a closed control loop, including means for generating high frequency electric energy, conversion means for converting the high frequency electric energy into ultrasonic energy, means for transmitting the ultrasonic energy into said reaction medium, means for measuring the effective ultrasonic energy in the reaction medium and for controlling said high frequency electric energy; and means for determining and maintaining the optimum frequency and intensity of said ultrasonic energy such as to provide for a desirable size parameter of the lipid vesicles, said determining and maintaining means including measuring means for measuring the actual value of a frequency and intensity of an ultrasonic field in the reaction medium obtained from said ultrasonic energy, and adjusting means for adjusting the intensity and frequency of said ultrasonic energy.

14. An arrangement as defined in claim 13, wherein said maintaining means is arranged to maintain the ultrasonic frequency and intensity so as to provide for a desirable size of the lipid vesicles.

15. An arrangement as defined in claim 13, wherein said maintaining means is arranged to maintain the ultrasonic frequency and intensity so as to provide for a desirable size distribution of the lipid vesicles.

16. An arrangement as defined in claim 13, wherein said measuring means includes a sound receiver which produces an output signal for adjusting the power and frequency of said generating means by said adjusting means.

17. An arrangement as defined in claim 16, wherein said sound receiver is formed as an acoustic-electric transducer.

18. An arrangement as defined in claim 17, and further comprising a tube, said acoustic-electric transucer being formed as a piezoelectric disk arranged at one end of said tube so that its sound-sensitive direction faces against said sound generating means.

19. An arrangement as defined in claim 13, wherein said sound generatic means includes an electric generator, said maintaining means including an actual value-nominal value comparator, and said adjusting means including an amplifier connected with said comparator and said electric generator.

20. An arrangement as defined in claim 13, wherein said sound generating means and said treatment container have geometries which are selected so as to avoid a reflection-caused formation of ultrasonic waves with a parameter deviating from a nominal parameter.

21. An arrangement as defined in claim 20, wherein the geometries of said sound generating means and said container are selected so as to avoid a formation of reflection-caused ultrasonic waves with a frequency deviating from a nominal frequency.

22. An arrangement as defined in claim 20, wherein the geometries of said sound generating means and said container are selected so as to avoid a formation of reflection-caused ultrasonic waves with a phase which is offset relative to a phase of primary ultrasonic waves.

23. An arrangement is defined in claim 13, wherein said treatment container has double walls with hollow spaces therein; and further comprising means for supplying a cooling medium into said hollow spaces of said double walls of said container.

24. An arrangement as defined in claim 13, wherein said treatment container is closed from an outer atmosphere; and further comprising means for supplying an inert gas into said container above the reaction medium.

25. An arrangement as defined in claim 13, wherein said container is formed as a sterile bag; and further comprising a further container in which said sterile bag with the reaction medium is arranged, and which is filled with a further fluid.

26. An arrangement as defined in claim 13, wherein said means for generating ultrasonic vibration comprises a plurality of electro-acoustic transducers positioned near the bottom of said container.

27. An arrangement as defined in claim 26, wherein said electro-acoustic transducers are arranged in a substantially horizontal row.

* * * * *